United States Patent [19]

Fergus

[11] Patent Number: 5,398,699
[45] Date of Patent: Mar. 21, 1995

[54] CONDOM

[76] Inventor: Thomas Fergus, 7 Campbell Avenue, Dee Why, New South Wales 2099, Australia

[21] Appl. No.: 139,612

[22] Filed: Oct. 20, 1993

Related U.S. Application Data

[63] Continuation of Ser. No. 935,514, Aug. 25, 1992, abandoned.

[30] Foreign Application Priority Data

Apr. 10, 1992 [AU] Australia ............................ 14914/92

[51] Int. Cl.⁶ ................................................ A61F 6/04
[52] U.S. Cl. ...................................... 128/844; 128/918
[58] Field of Search ................. 128/842, 844, 918; 604/347–353

[56] References Cited

U.S. PATENT DOCUMENTS

| | | | |
|---|---|---|---|
| D. 246,118 | 10/1977 | Okamoto | 128/844 |
| 2,586,674 | 2/1952 | Lönne | 128/844 |
| 3,363,624 | 1/1968 | Fishman | 128/844 |
| 3,536,066 | 10/1970 | Ludwig | 128/842 |
| 3,759,254 | 9/1973 | Clark | 128/844 |
| 4,961,734 | 10/1990 | Kassman | 128/844 |
| 4,966,166 | 10/1990 | Leffler | 128/918 |
| 5,027,831 | 7/1991 | Reddy | 128/844 |
| 5,109,871 | 5/1992 | Thornton | 128/844 |
| 5,111,831 | 5/1992 | Foggia | 128/842 |
| 5,176,152 | 1/1993 | Wheeler | 128/918 |

FOREIGN PATENT DOCUMENTS

| | | | |
|---|---|---|---|
| 0267218 | 11/1913 | Germany | 604/349 |
| 2519357 | 11/1976 | Germany | 128/844 |
| 9106268 | 5/1991 | WIPO | 128/844 |

*Primary Examiner*—Michael A. Brown
*Attorney, Agent, or Firm*—Leydig, Voit & Mayer, Ltd.

[57] ABSTRACT

This invention provides an improved condom of the type having a generally tubular body with an open end and a closed end. The tubular body has a concertina expander portion and an enlarged portion located between the concertina expanded portion and the open end. The enlarged portion tapers towards the open end.

11 Claims, 1 Drawing Sheet

CONDOM

"This is a continuation of application Ser. No. 07/935,514, filed on Aug. 25, 1992, now abandoned.

This invention relates to an improved condom. In particular, this invention provides a condom which has an enhanced ability to remain in place once fitted and which is not unnecessarily taut.

BACKGROUND OF THE INVENTION

Condoms for use as a means of preventing contraception or the spread of disease have been known for many years. Traditionally, a condom is formed from an elastomeric impermeable material and is generally tubular, with an open mouth at one end. Such a condom is usually marketed in rolled up configuration and is fitted to an erect penis by unrolling the condom. When properly fitted, the condom substantially covers the penis, with the open mouth of the condom located at or near the base of the penis.

Traditional condoms are of uniform cylindrical cross-section, except for perhaps a teat at the closed end, and are normally made by dipping a correspondingly shaped former into rubber latex or the like, to result in a sheath having thin walls of uniform thickness.

It is a notorious fact that traditional condoms often fail to remain in position and slip off the penis during use. In an effort to overcome this, some condoms are manufactured so that when fitted they grip the penis tightly. However, this in itself can cause problems: too taut a condom can give rise to discomfort.

It is an object of this invention to provide a condom which has an enhanced ability to remain on the penis once fitted and which is able to accomplish this aim while avoiding unnecessary tautness.

A further problem with traditional condoms is length. A condom of a particular diameter will not necessary cover all lengths of penis. Consequently, it is an object of this invention to provide an improved condom which is capable of covering a greater range of penis lengths than in the case of traditional condoms.

Another problem with traditional condoms arises because the condom must be stretched to fit so tightly around the penis, in order to stay in place during use, that there is no frictional movement between the walls of the condom and the penis. This is undesirable, since it can reduce sensations which may otherwise be available.

It is an object of this invention, in one preferred embodiment thereof, to provide an improved condom which not only has an enhanced ability to remain on the penis once fitted while avoiding unnecessary tautness, but also incorporates an enlarged portion to enhance relative sliding movement between the enlarged portion and part of the penis fitted with the condom.

BRIEF SUMMARY OF THE INVENTION

Accordingly, this invention provides an improved condom of the type having a generally tubular body with an open end and a closed end, characterised in that the tubular body has a concertina expander portion and an enlarged portion located between the concertina expanded portion and the open end, the enlarged portion tapering towards the open end.

Preferably, the condom of the invention is made of silicon rubber or similar material traditionally used for condom manufacture.

It is intended that in use the condom of the invention will be fitted over the penis and testicles of the user. For this purpose, the enlarged portion of the condom is intended to accommodate the testicles. The taper between the enlarged portion and the open end retains the condom in place, once fitted.

The open end is intended to encircle the base of the testicles in a sufficiently taut manner to retain the condom on the penis. It has been found that the area at the base of the testicles is relatively insensitive and any relative tautness of the open end in this area is of little consequence.

On the other hand, the design of the condom of the invention means that it is anchored at the base of the testicles rather than by tautness around the penis shaft. Consequently, there is no need for the condom to be uncomfortably taut around the penis shaft.

The new configuration of the condom of the present invention permits advantage to be taken of the fact that different regions of the penis are sensitive to different types of stimulation and hence contribute in different ways to overall erotic stimulation. Since the condom of the invention does not require that the tubular body be taut over the penis shaft, a larger range of erotic stimulation is made available.

Preferably, the enlarged portion comprises less than half the length of the tubular body.

In a preferred embodiment, the condom of the invention includes a second expanded portion located between the concertina expanded portion and the closed end, for permitting relative movement between the second enlarged portion and part of a penis fitted with the condom.

It will be apparent to one skilled in the art that the concertina expander portion permits the condom of the invention to fit a large range of penis lengths. The length of the penis to which the condom of the invention is fitted will determine the degree of expansion of the concertina expander portion.

BRIEF DESCRIPTION OF THE DRAWING

The invention will now be described with reference to a preferred embodiment as illustrated in the accompanying Drawing, in which.

DETAILED DESCRIPTION OF THE DRAWING

Figure 1:
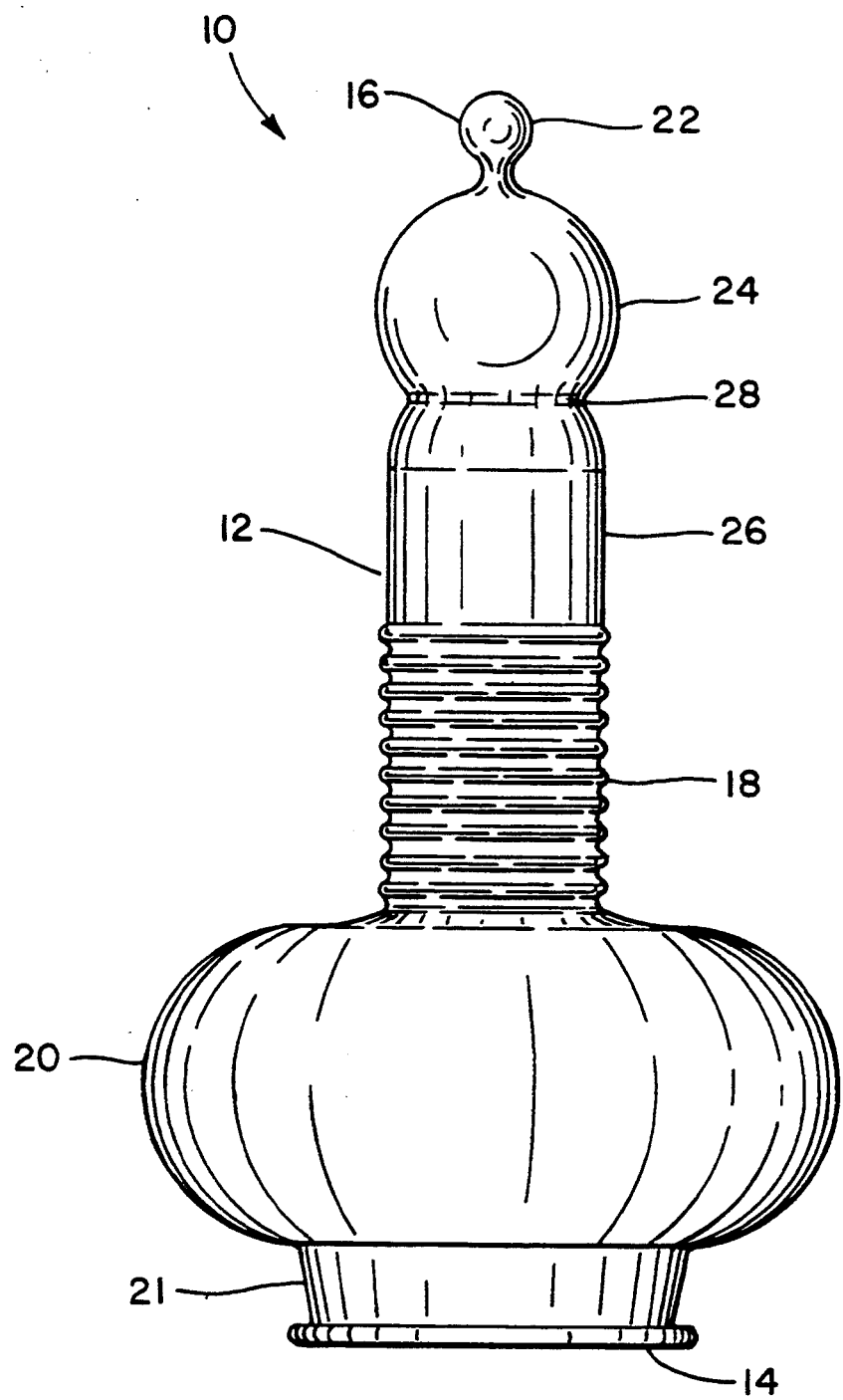
FIG. 1 represents a side elevational view of an embodiment of the condom of the invention.

In FIG. 1 the condom, indicated generally as 10, is a thin-walled rubber sheath having a generally tubular body 12 with an open end 14 and a closed end 16. Tubular body 12 has a concertina expander portion 18 and an enlarged portion 20 located between the concertina expander portion 18 and the open end 14. Enlarged portion 20 tapers into open end 14 as shown at 21.

Condom 10 also includes a teat 22 suitable for containing a germicidal lubricant inserted by the user, if desired, and a second enlarged portion 24 which is intended to slide over the head of the penis (not shown) on which the portion 24 is mounted. Between second enlarged portion 24 and concertina expander portion 18, tubular body 12 has a smoothly finished section 26. The illustrated embodiment in FIG. 1 also has a neck portion 28 located between the smooth section 26 and the closed end 16 having a smaller diameter than the smooth section 26 for holding the condom in place.

Typical dimensions for this embodiment of the invention are as follows: in unstretched configuration, taper 21 is 5–6 cm in length, first enlarged portion 20 is 4–5 cm, concertina expander portion 18 is 4–5 cm, smoothly finished section 26 is 3–4 cm and second enlarged portion 24 is 2–3 cm in length.

It will be appreciated that the description of the invention in connection with the Drawing is for the purpose of illustration only and is not intended to be limiting on the scope of the invention.

I claim:

1. An improved condom of the type comprising a generally tubular body with an open end and a closed end, characterized in that the tubular body has a concertina expander portion including a pleated cross-sectional shape that permits expansion to accommodate variable penis lengths wherein the pleats are substantially disposed along the lateral axis of the condom, a smooth body portion located between the concertina expander portion and the closed end, a neck portion located between the smooth body portion and the closed end having a smaller diameter than the smooth body portion for holding the condom in place, and an enlarged portion located between the concertina expanded portion and the open end, the enlarged portion tapering towards the open end to retain the condom in place.

2. The condom claimed in claim 1, wherein the condom is made of silicon rubber.

3. The condom claimed in claim 1, wherein in use the enlarged portion is adapted to accommodate testicles, the taper between the enlarged portion and the open end being adapted to retain the condom in place, once fitted.

4. The condom claimed in claim 3,, wherein the enlarged portion comprises less than half the length of the tubular body.

5. The condom claimed in claim 3,, wherein the includes a teat at the closed end.

6. An improved condom of the type comprising a generally tubular body with an open end and a closed end, characterized in that the tubular body has:

a concertina expander portion including a pleated cross-sectional shape that permits expansion to accommodate variable penis lengths wherein the pleats are substantially disposed along the lateral axis of the condom;

a first enlarged portion located between the concertina expanded portion and the open end, the enlarged portion tapering towards the open end to retain the condom in place;

a second enlarged portion located between the concertina expanded portion and the closed end, for permitting relative movement between the second enlarged portion and part of a penis fitted with the condom;

a smooth body portion located between the concertina expander portion and the second expanded portion; and a neck portion located between the smooth body portion and the closed end having a smaller diameter than the smooth body portion for holding the condom in place.

7. The condom claimed in claim 6, wherein the condom made of silicon rubber.

8. The condom claimed in claim 6, wherein in use the first enlarged portion is adapted to accommodate testicles, the taper between the first enlarged portion and the open end being adapted to retain the condom in place, once fitted.

9. The condom claimed in claim 8, wherein the first enlarged portion comprises less than half the length of the tubular body.

10. The condom claimed in claim 9, wherein the condom includes a teat at the closed end.

11. An improved condom of the type comprising a generally tubular body having open and closed ends, a concertina expander portion disposed between the open and closed ends having a pleated cross-sectional shape for permitting expansion to accommodate variable penis lengths wherein the pleats are substantially disposed along the lateral axis of the condom, an enlarged portion located between the concertina expanded portion and the open end and tapering towards the open end to retain the condom in place, a second enlarged portion located between the concertina expanded portion and the closed end for permitting relative movement between the second enlarged portion and part of a penis fitted with the condom, a smooth body portion located between the concertina expander portion and the second enlarged portion, and a neck portion located between the smooth body portion and the second enlarged portion having a smaller diameter than the smooth body portion for holding the condom in place.

* * * * *